United States Patent [19]

Eden

[11] 4,185,039
[45] Jan. 22, 1980

[54] SELECTIVE CATALYTIC OXIDATION OF CARBON MONOXIDE IN THE PRESENCE OF OLEFIN MONOMER

[75] Inventor: Jamal S. Eden, Akron, Ohio

[73] Assignee: B. F. Goodrich Company, Akron, Ohio

[21] Appl. No.: 972,770

[22] Filed: Dec. 26, 1978

[51] Int. Cl.² .................. C07C 21/00; C07C 11/00
[52] U.S. Cl. ..................... 260/654 A; 260/654 S; 585/848; 423/247
[58] Field of Search ............ 260/654 A, 654 S, 677 A

[56] References Cited

U.S. PATENT DOCUMENTS 3,549,719  12/1970  Duyverman .................. 260/677 A
4,113,786   9/1978  Tsao ........................... 260/654 A Primary Examiner—John F. Niebling
Attorney, Agent, or Firm—John H. Faro

[57] ABSTRACT

Process for the selective catalytic oxidation of carbon monoxide in the presence of olefin monomers without appreciable oxidation of such monomers. According to this process, a gaseous waste stream containing carbon monoxide, olefin monomers, and a variety of other agents, is contacted with a catalytically effective amount of copper chromite, preferably in an oxygen enriched environment, at temperatures in the range from about 200° C. to about 325° C. The contact time of the stream with the catalyst bed can vary within broad limits, and the duration of which will vary inversely with the temperature of the catalyst bed.

7 Claims, 1 Drawing Figure

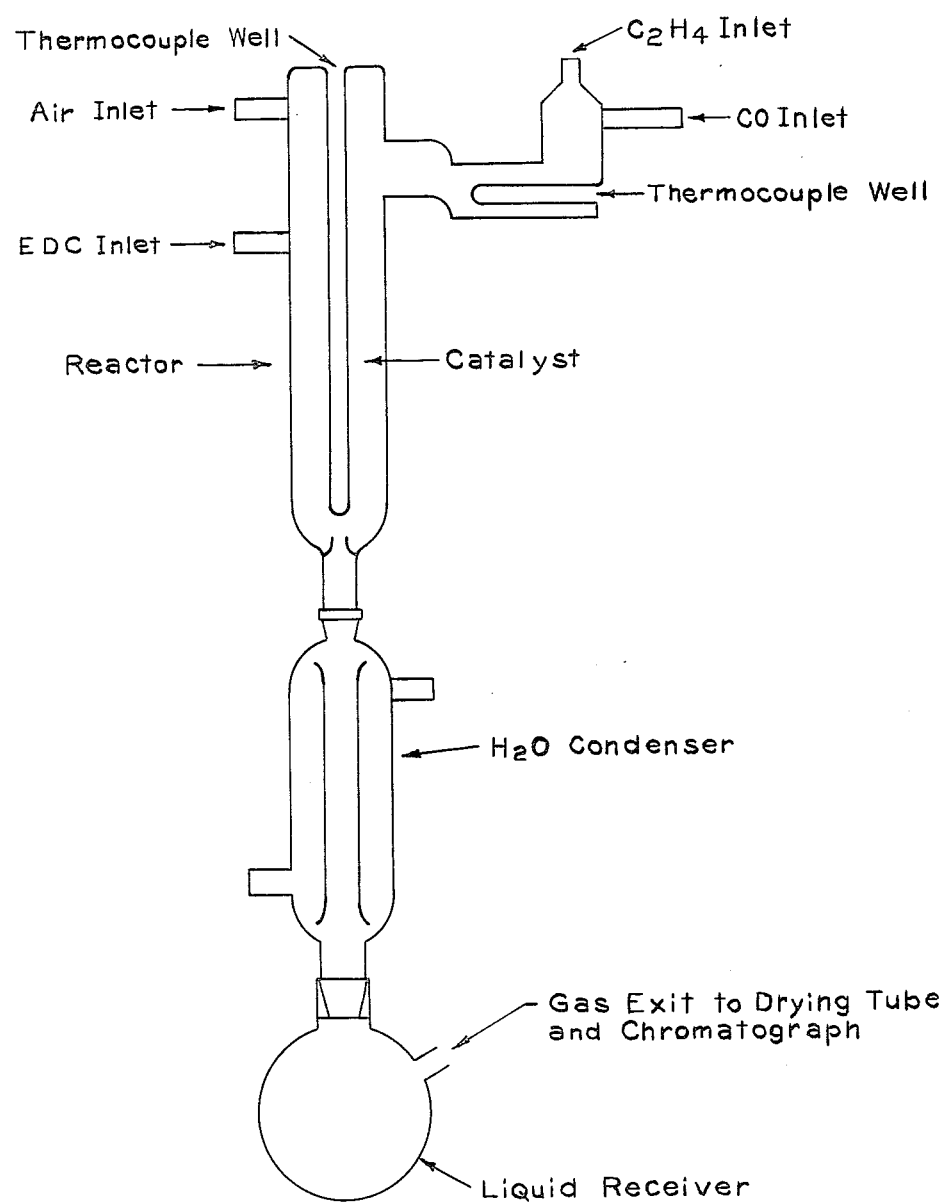
FIXED BED REACTOR

SELECTIVE CATALYTIC OXIDATION OF CARBON MONOXIDE IN THE PRESENCE OF OLEFIN MONOMER

BACKGROUND OF THE INVENTION

1. Field of the Invention

This invention relates to a process. More specifically, this invention is directed to the selective catalytic oxidation of carbon monoxide in the presence of hydrocarbons.

2. Description of the Prior Art

In the commercial manufacture of certain type of chlorinated hydrocarbons, ethylene, hydrogen chloride and oxygen are reacted with one another in the presence of an oxyhydrochlorination catalyst. The product resulting therefrom includes ethylene dichloride, which is a liquid, and certain gaseous materials, including ethylene. It is both desirable and economical to recycle unreacted materials from the waste stream and thus conserve raw materials and reduce disposal problems. As is readily appreciated, should the waste stream contain readily oxidizable materials, these materials will compete with the ethylene in the oxyhydrochlorination process, thereby substantially reducing the efficiency thereof. In addition, such competing reactions increase energy consumption. In order to avoid these problems and yet recapture many of the useful materials present in the waste stream, the prior art has previously attempted to recover these reactants by separation thereof prior to recycling back into the reactor environment. Such separation procedures are both costly and time-consuming and can substantially offset any savings realized from the recovery of these unreacted materials.

With ever increasing prices of feedstocks, there is a continuing need for cost-efficient techniques for recovery of unreacted materials which result from the synthesis of ethylene dichloride. In order for such recovery schemes to be economically feasible, it is necessary to achieve such recycling in a manner which minimizes capital equipment requirements and yet achieves as great a recovery of unreacted material as possible.

SUMMARY OF THE INVENTION

It is the object of this invention to remedy the above, as well as related deficiencies in the prior art.

More specifically, it is the principal object of this invention to provide a process for the selective catalytic oxidation of carbon monoxide in a waste stream containing olefin monomer, such as ethylene.

It is another object of this invention to provide a process for the selective removal of readily oxidizable materials from a recycle stream to be used in the synthesis of additional ethylene dichloride by oxyhydrochlorination of ethylene monomer.

It is yet another object of this invention to provide a process for enhancement in the efficiency of chlorohydrocarbon synthesis through essentially complete recycle of unreacted materials used in such synthesis.

The above related objects are achieved by providing a process for the selective catalytic oxidation of carbon monoxide in a waste stream containing olefin monomers. Such selective oxidation is achieved by contacting the waste stream with a catalytically effective amount of copper chromite at a catalyst bed temperature in the range of from about 225° to about 320° C. and preferably in an oxygen enriched environment. The contact time of the catalyst with the stream is limited to less than about one second, and preferably less than half a second; the duration of contact being inversely proportional to the temperature of the catalyst bed. The optimum conditions of this process provide for maximum oxidation of carbon monoxide without appreciable oxidation of the olefin monomer also present in the feedstream. In the preferred embodiments of this invention, chlorine-containing materials are initially separated from the waste stream prior to contact of the feedstream with the oxidation catalyst.

DESCRIPTION OF THE INVENTION INCLUDING PREFERRED EMBODIMENTS

As noted previously herein, in the commercial scale manufacture of ethylene dichloride by oxyhydrochlorination of ethylene, certain unreacted materials are present in the waste stream. It is desirable to recover as many of these unreacted materials as possible and yet preserve the efficiency of the process in which such recycled compounds are used. Accordingly, the waste stream containing the ethylene, hydrogen chloride, and carbon dioxide are initially passed through an absorbing medium, whereupon the hydrogen chloride is effectively and selectively removed from the waste stream. Prior removal of the hydrogen chloride is essential to prolonged oxidation catalyst activity. Subsequent to absorption of chlorine-containing compounds from the waste stream, the waste stream is contacted, at the appropriate temperature, with an oxidation catalyst. The oxidation catalyst suitable for use in this invention is copper chromite because of its selectivity with respect to the carbon monoxide component of the waste stream. The effectiveness of the catalyst in the oxidation of carbon monoxide is a function of the catalyst bed, the duration of contact between the catalyst and waste stream and the relative surface area of the catalyst which comes in contact with the waste stream.

The copper chromite catalyst suitable for use in the process of this invention is distinguishable from other oxidation catalysts in that its effectiveness in selective oxidation of carbon monoxide is achieved at temperatures as low as about 225° C. The copper chromite catalyst suitable for use in this process is available commercially from the Harshaw Chemical Company, Cleveland, Ohio (Harshaw Copper Chromite Catalyst Cu-Cr 576A-6-2-63 E ⅛").

Of course, at such lower temperatures the contact time between the waste stream and the catalyst bed must be substantially more than would be required at temperatures approaching 300° C. In the present commercial environment, it is desirable to minimize contact time, and thus the temperature of the catalyst bed is preferably maintained at between 275° and 300° C. in order to provide maximum throughput without appreciable oxidation of the ethylene component of the waste stream. In the context of this invention, an "appreciable amount" of ethylene is deemed to have been oxidized when the concentration of ethylene present in the waste stream is reduced more than ten percent (10%). This catalyst can be used, in the instant process, both as a fixed bed material and in a fluidized bed environment. In order to effect greater throughput of the waste stream and more efficient operation, the fluidized bed mode of operation is preferred.

The temperature at which the catalyst bed is maintained during selective oxidation of carbon monoxide is in the range of from about 225° to about 325° C. As noted previously herein, the contact time and temperature are related in that the amount of time required to effectively catalyze the oxidation of carbon monoxide to carbon dioxide is inversely proportional to the temperature of the catalyst bed. This feature is of vital importance in the context of this invention, since the oxidation of ethylene is highly temperature dependent, and thus the oxidation of carbon monoxide at or below about 300° C. will effectively preclude appreciable oxidation of the ethylene where the contact time between the waste stream and the catalyst bed is less than about 0.5 seconds, and preferably less than about 0.25 seconds.

It is advisable, although not essential, to absorb chlorinated materials from the waste stream prior to contact of the waste stream with the catalyst. This is achieved through the use of standard expedients for absorption of, for example, hydrogen chloride gas and other chlorinated gaseous compounds. Typically, this procedure involves passing the product stream through a hot quench column whereby the stream is contacted with water and caustic. The chlorinated hydrocarbons, including the hydrogen chloride gas, are thus separated from the product stream facilitating recycling of unreacted materials. The presence of substantial quantities of such chlorinated compounds will shorten the active life of the oxidation catalyst, and thus is to be avoided if at all possible. Of course, in the context of the instant invention the absorption of the chlorinated materials from the waste stream should be consistent with the recycling of such chlorinated materials, along with the ethylene, for the further production of ethylene dichloride.

The process of this invention can be readily exemplified by simple reference to FIG. 1, wherein a simulated waste stream was subjected to catalytic incineration in a Vycor fixed bed reactor at temperatures within the range shown in the following table. In a typical run, the catalyst bed was heated to the desired reaction temperature in the presence of air. The ethylene, carbon monoxide, and ethylene dichloride were fed through sidearms and preheated to between 250° and 300° C. The reaction was allowed to run for about two hours before samples were analyzed by gas chromatograph techniques. All analytical work was performed on gas chromatographs, using 810 F&M. When ethylene and carbon monoxide were in the feed, the product stream leaving the reactor was allowed to pass through a drierite tube (for absorption of moisture), then through heated lines leading directly to the gas chromatograph machine, to be analyzed by five A molecular sieves ($\frac{3}{4}$ m × $\frac{1}{4}$″) and Porapak S (6′ × $\frac{1}{4}$″) columns connected in series. In this way, the oxygen, nitrogen, methane and carbon monoxide were separated on five A molecular sieves and carbon dioxide and ethylene were separated on the Porapak S. When EDC was part of the feed, the product stream leaving the reactor was bubbled through 200 milliliters of distilled water at 70° C. to remove HCl, then through the drierite tube, and thereafter through heated lines to the gas chromatograph for analysis in the manner described above. The analysis of ethylene, vinyl chloride, and EDC was performed on a Hewlett-Packard 5750 hydrogen flame ionization apparatus. As is evident from the following table, essentially complete conversion of carbon monoxide to carbon dioxide is achieved at a temperature approaching 325° C. Under the conditions specified hereinabove, some ethylene is also oxidized.

TABLE I

Oxychlorination Vent-Catalytic Incineration

Organic Feed (OF): $C_2H_4$ + CO
Catalyst: Harshaw Copper Chromite, Cu-Cr 576A-6-2-63 E $\frac{1}{8}$″
Conditions: $C_2H_4$ + CO in feed = 0.94%;
  $O_2$ in feed = 10.7% ($N_2$ diluent);
  $C_2H_4/CO/O_2/N_2$ = 1/.81/20.8/167.9

| Temp. °C. | C.T. sec. (hot) | Conversion, % $C_2H_4$ | CO | $C_2H_4$ (out) ppm | Carbon Balance % | Time Elapsed Hours |
|---|---|---|---|---|---|---|
| 281 | 0.167 | 0 | 53.3 | 7505 | 107 | 6 |
| 335 | 0.152 | 30.1 | 100 | 5073 | 107 | 25 |
| 390 | 0.139 | 62.0 | 100 | 2739 | 108 | 27 |
| 430 | 0.131 | 79.5 | 100 | 1480 | 107 | 28 |
| 480 | 0.122 | 93.8 | 100 | 597 | 107 | 30 |
| 515 | 0.117 | 97.8 | 100 | 375 | 99 | 51 |
| 560 | 0.111 | 100 | 100 | 193 | 99 | 53 |
| 604 | 0.105 | 100 | 100 | 70 | 100 | 54 |
| 650 | 0.100 | 100 | 100 | 49 | 100 | 74 |
| 678 | 0.097 | 100 | 100 | 37 | 99 | 78 |

I claim:

1. A process for the selective oxidation of carbon monoxide in a gaseous stream containing olefin monomer, said process comprising contacting said stream with a catalytically effective amount of copper chromite at a bed temperature in the range of from about 250° to about 320° C. the interval of contact of the stream with the catalyst being less than one second and the duration of contact being inversely proportional to temperature of the catalyst bed, so as to effect maximum oxidation of carbon monoxide without appreciable oxidation of the olefin monomer present in said stream.

2. The process of claim 1, wherein the stream subsequent to selective catalytic oxidation of carbon monoxide, is recycled, essentially intact, to a reactor wherein the olefin monomer is reacted with appropriate quantities of hydrogen chloride and oxygen in the presence of an oxyhydrochlorination catalyst, thereby forming at least some chlorohydrocarbon compounds.

3. The process of claim 1, wherein the olefin monomer is ethylene.

4. The process of claim 2, wherein the olefin monomer is ethylene and the chlorohydrocarbon product includes ethylene dichloride.

5. The process of claim 1, wherein the temperature of the bed is up to about 300° C. and the contact time is less than about 0.25 seconds.

6. The process of claim 2, wherein the temperature of the bed is up to about 300° C. and the contact time is less than about 0.25 seconds.

7. In a process for the synthesis of ethylene dichloride by catalytic oxyhydrochlorination of ethylene wherein, as an incident to such synthesis, a gaseous waste stream is produced containing carbon monoxide, hydrogen chloride, and ethylene, and such stream is recycled to produce additional ethylene dichloride, the improvement comprising:

separating chlorine containing compounds from said waste stream and thereafter contacting said stream with a catalytically effective amount of copper chromite at a bed temperature in the range of from about 250° to about 320° C., the interval of contact being less than one second and the duration of contact being inversely proportional to the catalyst bed so as to effect maximum oxidation of carbon monoxide without appreciable oxidation of the olefin monomer.

* * * * *